US007218767B2

(12) United States Patent
Eck

(10) Patent No.: US 7,218,767 B2
(45) Date of Patent: May 15, 2007

(54) METHOD OF IMPROVING THE RESOLUTION OF A MEDICAL NUCLEAR IMAGE

(75) Inventor: Kai Eck, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 840 days.

(21) Appl. No.: 10/323,146

(22) Filed: Dec. 18, 2002

(65) Prior Publication Data

US 2003/0114743 A1 Jun. 19, 2003

(30) Foreign Application Priority Data

Dec. 19, 2001 (DE) ............... 101 62 273

(51) Int. Cl.
*G06K 9/00* (2006.01)
(52) U.S. Cl. .................. 382/138; 382/285; 600/407
(58) Field of Classification Search ............... 382/128, 382/129, 130, 131, 132, 133, 134, 168, 171, 382/173, 203, 255, 256–257, 260, 274, 275, 382/294, 305, 285; 600/431, 454, 407, 587; 345/421; 378/4
See application file for complete search history.

(56) References Cited

U.S. PATENT DOCUMENTS

| 4,737,921 | A | * | 4/1988 | Goldwasser et al. | ......... | 345/421 |
| 5,524,636 | A | * | 6/1996 | Sarvazyan et al. | .......... | 600/587 |
| 5,839,440 | A | * | 11/1998 | Liou et al. | .................. | 600/431 |
| 5,871,013 | A | * | 2/1999 | Wainer et al. | ............... | 600/407 |
| 6,464,642 | B1 | * | 10/2002 | Kawagishi | .................. | 600/454 |

OTHER PUBLICATIONS

J.B.Antoine Maintz and Max A. Viergever; A Survey of Medical Image Registration; Oxford University Press, Oxford, GB, vol. 2, No. 1, 1998, pp. 1-37.
P.A. Van Den Elsen et al.; Grey Value Correlation Techniques Used for Automatic Matching; Proc. Visualization in Biomedical Computing; vol. 2359, Oct. 1994, pp. 227-237.
J.P. Caravel, et al.; "Fusion d'images anatomique (echographie) et fonctionnelles (tomoscintigraphie) renales" Medecine Nucleaire, 1995, Elsevier.

* cited by examiner

*Primary Examiner*—Seyed Azarian
(74) *Attorney, Agent, or Firm*—Douglas B. McKnight

(57) ABSTRACT

The invention relates to a method of improving the precision of a medical nuclear SPECT or PET image in which notably a nuclear sectional image (n) can be superposed on a two-dimensional ultrasound image (u). For the superposition that nuclear sectional image ($n_0$) which exhibits the best correspondence with a free-hand ultrasound image (u) is chosen from a three-dimensional nuclear image (2). In order to determine this sectional image, an evaluation index f(n,u) is calculated, on the basis of an estimated value (1), for differently situated nuclear sectional images (n). This index assigns a positive value to positions of structures (heart muscle tissue etc.) which correspond in the two images, a neutral value to structures which are represented only in the ultrasound image (u) and a negative value to structures which are represented only in the nuclear sectional image (n). The nuclear sectional image ($n_0$) having the highest value of the evaluation index is subsequently displayed so as to be superposed on the ultrasound image. In a generalized form the method can also be carried out in conjunction with three-dimensional ultrasound images.

19 Claims, 2 Drawing Sheets

METHOD OF IMPROVING THE RESOLUTION OF A MEDICAL NUCLEAR IMAGE

BACKGROUND

The invention relates to a method of improving the resolution of a medical nuclear image of a body volume by combining it with an ultrasound image of the same body volume. The invention also relates to a device which includes a memory and a data processing unit and is suitable for carrying out such a method.

Medical nuclear methods have become very prominent in medical diagnostics, because they enable the visualization of body functions via observation of the absorption of radioactive marker substances. Hereinafter SPECT (Single Photon Emission Computed Tomography) and PET (Positron Emission Tomography) will be considered by way of example. These methods yield three-dimensional representations of the metabolic activity of the heart muscle, but these images have a comparatively poor spatial resolution so that an exact diagnosis of the heart function is impeded in many cases.

On the other hand, it is known that sectional images of the heart can be acquired with a favorable resolution by means of ultrasound methods. In the case of ultrasound operation in the so-called B mode, a sound wave having a pronounced directional characteristic is applied to the tissue. The echo signal reflected by the tissue is demodulated, logarithmated and stored. Subsequently, a new sound wave is applied along a different trajectory which, like all previous sound wave trajectories, however, is situated in the plane to be imaged. After the plane has been sufficiently densely scanned in this manner, the demodulated and logarithmated echoes are encoded as grey values and arranged in the image plane in such a manner that an image of the objects in the scanned plane is obtained which is faithful in respect of length and angle. The described scanning of the plane can be performed by means of a fan-shaped, parallel or other configuration of the sound wave trajectories. An ultrasound image of a volume can be obtained by selecting the trajectories of the sound waves to be such that they are not situated in one plane but scan a volume (for example, conically or by parallels). It is a common aspect of the ultrasound images that they represent only the anatomy and not the function of the heart muscles.

Furthermore, from literature (J. P. Caravel et al., Fusion d'images anatomique (échographie) et fonctionnelles (tomoscintigraphie) rénales, MÉDECINE NUCLÉAIRE, 1995, Elsevier) a method is known for the imaging of the kidneys of a patient; according to this method first a three-dimensional scintigraphic image and subsequently a two-dimensional ultrasound image are formed of the kidneys. In that case the ultrasound apparatus is provided with position markers (light-emitting diodes) which are detected by a camera system so as to be related to a stationary reference system. The position in space of the ultrasound apparatus or the ultrasound image as well as the position of the scintigraphically imaged body volume are then determined by way of appropriate calculations; subsequently, a sectional image corresponding to the ultrasound image can be calculated from the three-dimensional scintigraphic image so as to be superposed on the ultrasound image. Such a method has the drawback, however, that a large amount of work is required for the optical sensing of the position of the ultrasound apparatus and the scintigraph. Furthermore, the precision of the method is limited by the precision of the optical position sensing. Moreover, a systematic error effect is introduced by the fact that a motion of the patient, for example, due to respiration, may take place between the image acquisitions, so that imaging may be based on incorrect assumptions in respect of position.

SUMMARY

Considering the foregoing it is an object of the present invention to provide a device and a method for combining an ultrasound image with a medical nuclear image which offers greater accuracy of the registration and can be realized while utilizing a smaller amount of special hardware.

The method in accordance with the invention for improving the resolution or accuracy of a medical nuclear image is based on the combination of an ultrasound image of a body volume with the medical nuclear (often referred to hereinafter as nuclear image for the sake of brevity) of the same body volume. In accordance with the invention various assumed relative positions in space of the nuclear image and the ultrasound image are examined so as to find the relative position which (best) corresponds to reality. For each assumed relative position a nuclear sub-image, being a real part or a non-real part of the nuclear image, is compared with an ultrasound sub-image which is a real part or a non-real part of the ultrasound image; the nuclear sub-image and the ultrasound sub-image should then represent the same spatial section of the body volume for the assumed relative position. This comparison is performed quantitatively by calculation of an evaluation index for the correspondence between the nuclear sub-image and the ultrasonic sub-image. After completion of the calculations, the relative position having the optimum value of the evaluation index is chosen as the (real) spatial registration position of the nuclear sub-image and the ultrasound sub-image. Depending on the definition of the evaluation index, a high degree of correspondence can be represented by a particularly high value or a particularly low value, so that the optimum value of the evaluation index is to be understood as the maximum and the minimum, respectively, of all values obtained. Hereinafter, the normal convention will be followed, meaning that a large positive value of the evaluation index indicates a high degree of correspondence; however, all embodiments can be rendered compatible with alternative definitions in an analogous way.

A preferred version of the method concerns the case where the ultrasound image is a two-dimensional image which is identical to the respective ultrasound sub-images considered, and that the nuclear sub-images are derived as two-dimensional nuclear sectional images from a three-dimensional medical nuclear image. The comparison of a two-dimensional ultrasound image with a two-dimensional sectional image derived from a three-dimensional nuclear image relates to a situation which often occurs in practice and is, therefore, of particular relevance. Therefore, this situation is used, by way of example, in many of the following cases.

The method in accordance with the invention, however, also comprises a comparison of, for example, three-dimensional ultrasound images with two-dimensional or three-dimensional nuclear images. The comparison of each time three-dimensional images can then be performed via nuclear sub-images or ultrasound sub-images representing two-dimensional sections of the three-dimensional images. Notably sub-images consisting of three mutually orthogonal sections can be observed.

The described method offers the advantage that it does not require complex equipment for determining the relative position in space of the ultrasound image and the nuclear image. This position is determined instead with the aid of the evaluation index on the basis of the data already present. For example, in a three-dimensional medical nuclear image of the body volume that nuclear sectional image is searched which best matches a predetermined two-dimensional ultrasound image, the attending physician having complete freedom in selecting the sectional plane of the ultrasound image. A further advantage of the method consists in that it is robust to a high degree in respect of motion of the patient between the medical nuclear exposure and the ultrasound exposure, because this motion cannot lead to an incorrect assumption in respect of the relative position.

In accordance with said method the medical nuclear image of the body volume is preferably acquired by means of a SPECT or a PET method. These methods can provide the physician with valuable information, for example, concerning the metabolic function of the heart muscle; however, these methods both have the drawback of a comparatively poor spatial resolution. This drawback can be effectively mitigated by means of the proposed combination method.

In conformity with a preferred version of the method an estimated value is provided for the position of the ultrasound image relative to the body volume and the calculation of the evaluation index takes into account only those relative positions of the nuclear image and the ultrasound image where the nuclear image occupies an assumed position in a vicinity of this estimated value. This means that, for example, for the comparison of a three-dimensional nuclear image with a two-dimensional ultrasound image the angles which define the position of the nuclear sub-images (nuclear sectional images) are selected from a more or less large range around the corresponding estimated angle values. The amount of calculation work required can thus be reduced and also the risk of incorrect results. The estimated value for the position of the ultrasound image can be manually selected by the attending physician; for this purpose the physician may use customary exposure classifications (in the case of the heart, for example, "parasternal view along the longitudinal axis", "view of the aortic valve along the minor axis", "apical two-ventricle view", "left parasternal view along the longitudinal axis"). It is also feasible to utilize automatic methods for determining the estimated value; such automatic methods need not necessarily have a high accuracy.

Furthermore, a characteristic region is preferably selected from the ultrasound image; the subsequent calculation of the evaluation index is then performed exclusively in this selected region. All other image regions are of no importance for the evaluation of the correspondence between ultrasound sub-images and nuclear sub-images. The effect of irrelevant or falsified image regions on the registration between ultrasound sub-image and nuclear sub-image can thus be avoided. Notably regions with strong masking of the echo or with artefacts can thus be excluded from the ultrasound image. A further advantage of the limitation to a characteristic region resides in the reduction of the amount of calculation work required for the determination of the evaluation index.

In conformity with a further version of the method evaluation indices are calculated also for image combinations where at least one dimension of the ultrasound sub-image is expanded or compressed relative to the nuclear sub-image. Notably versions of the ultrasound image which are expanded/compressed+10% in the axial direction of the image can thus be corrected for errors caused by incorrect assumptions as regards the ultrasound speed.

In order to minimize the amount of calculation work required for determining the evaluation indices, the digital resolution of the ultrasound image and/or the nuclear image can be reduced prior to the calculation. Furthermore, the digital resolutions of the two types of image are advantageously equalized.

A preferred version of the method in accordance with the invention is characterized in that the evaluation index between the ultrasound sub-images and the nuclear sub-images is calculated as the sum over all corresponding image points (that is, image points of the ultrasound sub-image and the nuclear sub-image which are assumed to belong to the same point in space), each summand being assigned a high positive value if the compared image points of the ultrasound sub-image and the nuclear sub-image both represent a relevant structure;

being assigned a small value if only the image point of the ultrasound sub-image represents a relevant structure;

being assigned a high negative value if only the image point of the nuclear sub-image represents a relevant structure.

The method may notably be characterized in that a) the image point values of the ultrasound image are defined in such a manner that image points which belong to relevant structures have large image point values. This is so in the case of the customary gray value representation of ultrasound images in which the heart muscle tissue is represented in bright form, that is, in a representation with large gray values.

b) the image point values of the nuclear image are defined in such a manner that image points which belong to the relevant structures mentioned sub a) have large image point values when the structure is represented in the specific medical nuclear imaging method and small image point values when the structure is not represented. Such a definition is customary for SPECT or PET methods where a radioactive radiation activity is represented in bright form, that is, with large gray values.

c) the evaluation index between an ultrasound sub-image and a nuclear sub-image is calculated as the sum over all corresponding image points, each summand occurring in the sum and belonging to two corresponding image points:

being assigned a high positive value when the compared image points of the ultrasound sub-image and the nuclear sub-image both have large image point values;

being assigned a small (positive or negative, near zero) value when the image point of the ultrasound sub-image has a large image point value and the corresponding image point of the nuclear sub-image has a small image point value;

being assigned a large negative value when the image point of the ultrasound sub-image has a small image point value and the corresponding image point of the nuclear sub-image has a large image point value.

A method of this kind can be performed by means of the customary representations of an ultrasound image and a nuclear image in which structures detected by means of an ultrasound echo and radioactive radiation, respectively, are reproduced with large gray values (image point values). However, it is to be understood that an equivalent operation is also feasible when other representations are used. The method is based on the assumption that relevant (anatomical) structures are reproduced in any case in the ultrasound image and hence have large image point values. In the nuclear image, however, such anatomical structures are reproduced only if they exhibit an activity which can be detected by way of a nuclear exposure. Large image point values in the nuclear image, therefore, can in all cases be attributed to the presence of a relevant structure, whereas low image point values (dark areas) can be attributed to the absence of structures as well as to the physiological inactivity of structures present. This understanding is taken into account in the above definition of the evaluation index in that detection of corresponding relevant structures in the ultrasound sub-image and the nuclear sub-image is assigned a high positive value, that detection of a structure only in the ultrasound image is evaluated neutrally by way of a small value, and that the detection of a structure in the nuclear sub-image only is "penalized" by way of a large negative value, because it is in contradiction with the assumption of a spatial registration of the images observed.

In conformity with a further version of the latter method the large positive values and large negative values of the summands mentioned therein are assigned a larger absolute value the more reliably the image point values involved point to the relevant structure, that is, the larger the associated image point values are (when using the customary definition of the image point values). It is thus achieved that reliably recognized structures contribute as much as possible to the calculated evaluation index.

The described method can be used notably so as to display the selected nuclear sub-image in combination with the ultrasound sub-image. For example, the nuclear sub-image can be superposed in color on the ultrasound image.

Such a superposed display is preferably performed in the form of masking, that is, only in the positions in which the image point values of the ultrasound sub-image are larger than a predetermined value. In the case of an examination of the heart the nuclear sub-image would thus be superposed only in the positions in which the ultrasound sub-image shows heart muscle tissue.

The invention also relates to a device for the (two-dimensional or three-dimensional) imaging of a body volume, which device includes
a memory for an ultrasound image of the body volume;
a memory for a medical nuclear image of the body volume;
a data processing unit which is arranged to calculate, for various assumed relative positions of the medical nuclear image and the ultrasound image, an evaluation index concerning the correspondence of each time a nuclear sub-image and an ultrasound sub-image of the same section of the body volume and to select the relative position which has the optimum value of the evaluation index as the spatial registration position of the nuclear sub-image and the ultrasound sub-image.

A device of this kind is suitable for carrying out the described method in accordance with the invention and hence enables an improvement of the accuracy of medical nuclear images to be achieved. The device can be arranged, notably by appropriate programming of the data processing unit, in such a manner that it enables the execution of the various further versions of the method. Furthermore, the device may include a direct coupling to an ultrasound acquisition apparatus and/or a tomography apparatus for a SPECT or a PET method in order to take over images directly therefrom. The following description, claims and accompanying drawings set forth certain illustrative embodiments applying various principles of the present invention. It is to be appreciated that different embodiments applying principles of the invention may take form in various components, steps and arrangements of components and steps. These described embodiments being indicative of but a few of the various ways in which some or all of the principles of the invention may be employed in a method or apparatus. The drawings are only for the purpose of illustrating an embodiment of an apparatus and method applying principles of the present invention and are not to be construed as limiting the present invention.

DESCRIPTION OF THE DRAWINGS

The foregoing and other features and advantages of the present invention will become apparent to those skilled in the art to which the present invention relates upon consideration of the following detailed description of apparatus applying aspects of the present invention with reference to the accompanying drawings, wherein.

DESCRIPTION

Figure 1:
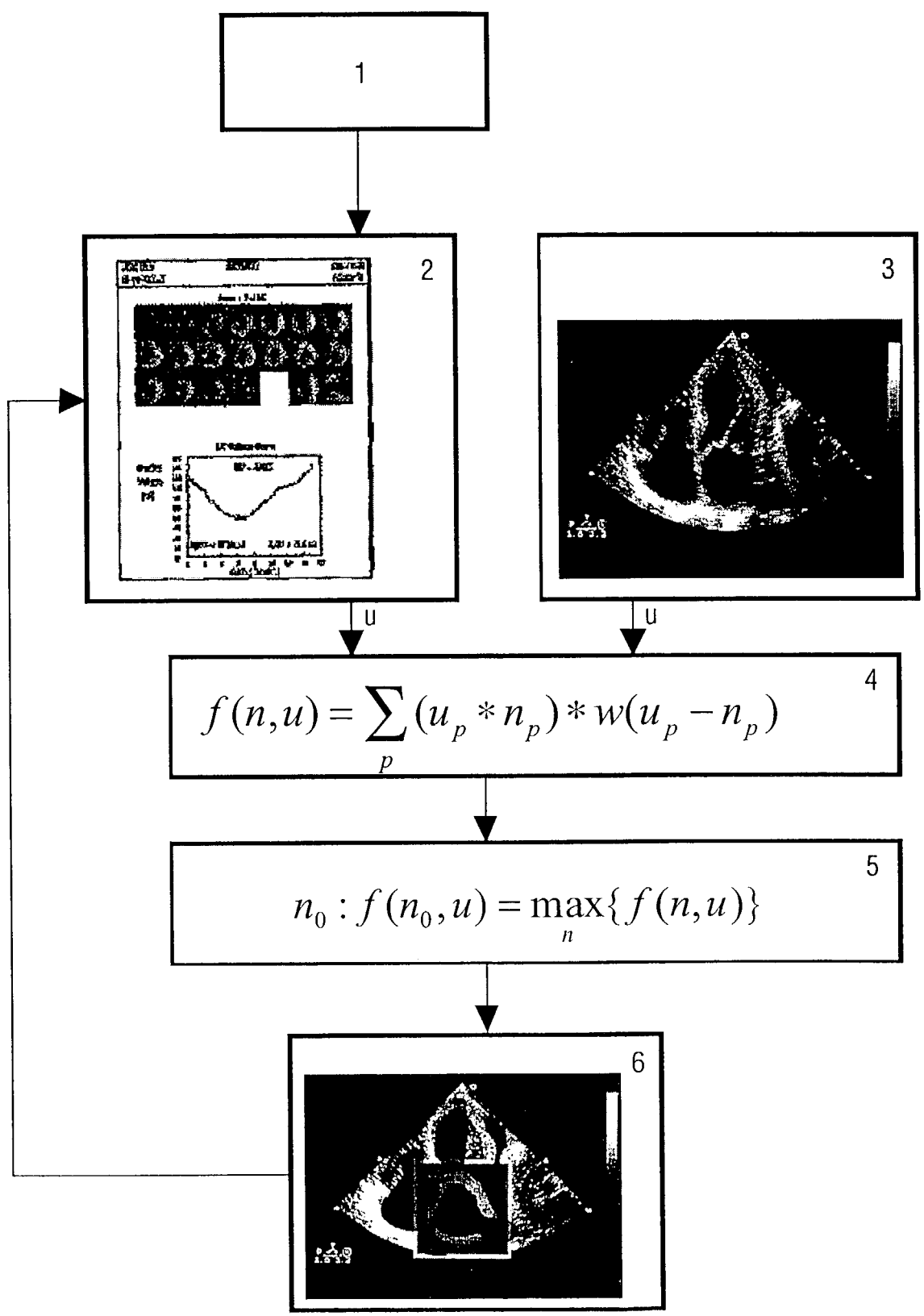
FIG. 1 shows a flow chart of a method in accordance with the invention for combining a two-dimensional ultrasound image with a two-dimensional sectional image from a three-dimensional medical nuclear image.

The method in accordance with the invention is intended to combine an ultrasound image of the heart, offering a high spatial resolution, with a nuclear image which enables the reproduction of physiological functions with a low spatial resolution. For the following example it is assumed that the ultrasound image is a two-dimensional image and that the nuclear image is a three-dimensional image.

For the desired combination first a standard medical nuclear method such as SPECT or PET is used to acquire the spatial representation of a body volume containing the heart as indicated in block 2. After the formation of this three-dimensional image, the physician utilizes a conventional, freely movable ultrasound apparatus without further special hardware so as to form a three-dimensional ultrasound image u of the heart (block 3). Furthermore, the physician can manually enter the approximate position of this ultrasound image relative to the heart (block 1).

After the presentation of the ultrasound image u, the three-dimensional medical nuclear image (block 2), and the initial or estimated value for the position of the ultrasound image (block 1), the determination of the section no of the nuclear volume image which best fits the ultrasound image u can commence. To this end, in block 2 two-dimensional sectional images n through the three-dimensional image volume are calculated. In advance some sectional images are calculated from a volume around the estimated value for the position of the ultrasound image. This means that a given bandwidth of feasible section positions around the estimated position of the ultrasound image u is considered so as to be compared with the ultrasound image u.

In order to determine the sectional image no which best fits the ultrasound image u (corresponding to the "ultrasound sub-image" of the general part of the description), subsequently the following steps are performed on the ultrasound image u and every comparative nuclear sectional image n (corresponding to the "nuclear sub-image" of the general part of the description):

1. The nuclear sectional image n is reduced in respect of resolution in order to reduce the amount of calculation work required for the image registration.

2. In the ultrasound image u a region of interest is selected, automatically or by hand, in order to exclude regions with strong masking of the echo or with artefacts.
3. The resolution of the ultrasound image u is reduced in such a manner that it corresponds to that of the nuclear sectional image n.
4. The comparison of the sectional image n and the ultrasound image u as performed in block 4 is based on the assumptions that:
   the ultrasound image u represents the heart muscle with larger gray values of the image points than the surrounding tissue and notably the lumen of the heart;
   the nuclear sectional image n shows a part of the heart muscle, be it that there may also be parts of the muscle which are not represented in the image. Taking into account the above considerations, in the registration algorithm an evaluation index f(n,u) is calculated which assigns a positive value to regions in which tissue is visible in the ultrasound image u as well as in the nuclear sectional image n; it evaluates zones in which tissue is visible only in the ultrasound image u as being neutral and it evaluates regions in which tissue is visible only in the nuclear sectional image n as being negative. Furthermore, the calculated evaluation index is locally weighted by the amplitude of the image signals of the images involved. It is assumed in this respect that the ultrasound image u and the nuclear sectional images n have been suitably prepared in respect of the mean value and the variance.
5. The evaluation index calculated as described in block 4 is compared with the maximum evaluation index obtained from the preceding calculations in the block 5. If it is larger than said maximum evaluation index, its value is stored as the maximum evaluation index obtained and the underlying nuclear sectional image n exhibits the best correspondence with the ultrasound image u thus far. The method then returns to the block 2 in which the next nuclear sectional image n is selected for the next comparison, said next nuclear sectional image occupying a slightly different position in the spatial imaging volume than the preceding sectional images.

In order to avoid incorrect registration due to a false assumption in respect of the ultrasound speed, the ultrasound image u can be expanded up to 10% in the axial direction prior to the calculation of the evaluation index in the block 4.

After all relevant nuclear sectional images n have been compared with the (expanded) ultrasound image u, the block 5 yields a sectional image no exhibiting the best correspondence. This image is superposed in block 6 on a rendition of the ultrasound image, so that the attending physician is presented the spatial information with a high resolution from the ultrasound image available as well as the physiological information from the medical nuclear image.

For the combined display the nuclear image n can be displayed as a colored overlay on the ultrasound image. Preferably, it is then reproduced as a mask, that is, only in the positions in which the ultrasound image shows heart tissue. Evidently, other compromises are also feasible between these two types of display.

A possible definition of the evaluation index f(n,u) used in the block 4 will now be described in detail with reference to the FIGS. 2 and 3.

Figure 2:
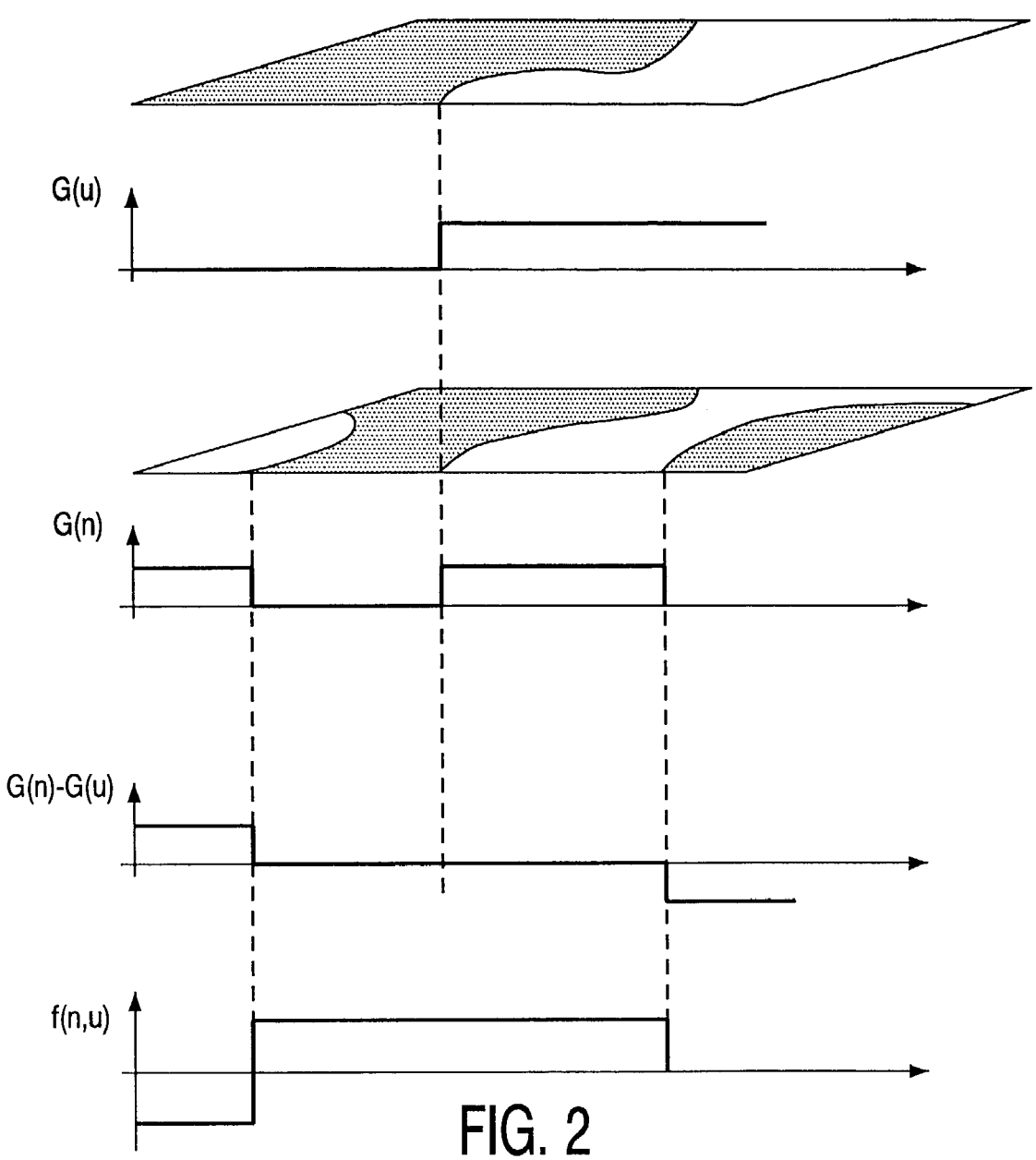
FIG. 2 illustrates the principle of the calculation, for one image point after the other, of an evaluation index for the correspondence between an ultrasound sub-image and a nuclear sub-image.
Figure 3:
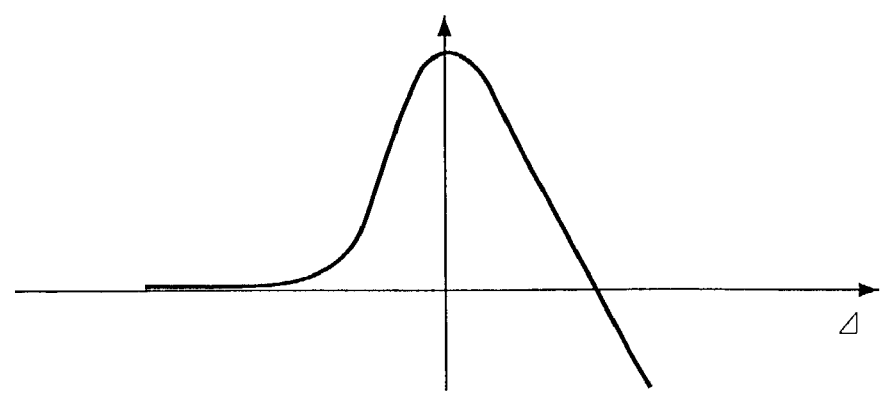
FIG. 3 shows the principle of the function used for the calculation of the evaluation index.

In FIG. 2 small sections of an ultrasound image u and a nuclear sectional image n to be registered are diagrammatically shown one underneath the other. For the purpose of simplification a black and white representation of the images is assumed. The heart muscle tissue of interest appears in bright form in the ultrasound image u, corresponding to a large grey value G(u) (vertical axis of the two-dimensional diagrams). Analogously, an observed radioactivity, based on a physiological activity in the tissue, appears in bright form in the nuclear sectional image n and hence as large grey values G(n).

The second diagram from the bottom in FIG. 2 shows a one-dimensional section which represents the difference between the gray values of the nuclear sectional image n and the ultrasound image u, that is, G(n)–G(u). Therein:
regions in which only the nuclear sectional image n shows tissue are positive,
regions in which the nuclear sectional image n and the ultrasound image u correspond as regards the presence or absence of tissue are zero, and
regions in which only the ultrasound image u shows tissue are negative.

If the nuclear sectional image n and the ultrasound image u were to have exactly the same position in space, the ultrasound image u should also show tissue in all locations where the nuclear sectional image n shows tissue, and in all locations where the ultrasound image u does not show tissue the nuclear sectional image should not show tissue either. Regions in conformity with these conditions, therefore, should be assigned a high or positive value in the evaluation index. Regions in which only the nuclear sectional image shows tissue should analogously be assigned a negative value. Zones in which only the ultrasound image u shows tissue leave the possibility of spatial correspondence open and, therefore, should be evaluated neutrally. A function f(n,u) which satisfies these criteria as shown in the lowermost diagram of FIG. 2 is defined, for example, as $$f(n, u) = \sum_p (u_p \cdot n_p) \cdot w(u_p - n_p)$$

where
p=image point
$u_p$=image point value of the image point p of the ultrasound image u
$n_p$=image point value of the image point p of the nuclear sectional image n.

The function $w(\Delta)$ is a weighting function which assigns a neutral value to large negative differences between n and u, a positive value to small differences and a negative value to large positive differences. For example, it may be defined as:

$$w(\Delta)=w(\Delta'+e)=a \cdot [1+b \cdot \sigma(c\Delta') \cdot (1-d\Delta' \cdot h(\Delta'))],$$

where $\Delta'=(\Delta)-e$, $\sigma(\Delta')$ is a Sigmoid function (continuous, monotonously increasing, extending through the origin of the co-ordinate system and having limit values –1 in the negative direction and +1 in the positive direction), and $h(\Delta')$ is the heavy side function (0 for x<0 and 1 for x>0), and in which the real numbers a, b, c, d, e>0 are matching parameters. The parameter e is preferably chosen to be such that the function $w(\Delta)$ has its maximum for $\Delta=0$. The variation principle of the weighting function w is shown in FIG. 3.

The invention is of course not limited to the described or shown embodiments, but generally extends to any embodiment, which falls within the scope of the appended claims as seen in light of the foregoing description and drawings. While a particular feature of the invention may have been described above with respect to only one of the illustrated embodiments, such features may be combined with one or more other features of other embodiments, as may be desired and advantageous for any given particular application. From the above description of the invention, those skilled in the art will perceive improvements, changes and modification. Such improvements, changes and modification within the skill of the art are intended to be covered by the appended claims.

Having described a preferred embodiment of the invention, the following is claimed:

1. A method of improving the resolution of a medical nuclear image of a body volume by combining it with an ultrasound image of the same body volume, the method comprising for various assumed relative positions of the nuclear medical image and the ultrasound image each time an evaluation index concerning the correspondence of a nuclear sub-image and an ultrasound sub-image of the same region of the body volume is calculated, and the relative position having the optimum value of the evaluation index is selected as the spatial registration position of the nuclear sub-image and the ultrasound sub-image; wherein the evaluation index between an ultrasound sub-image and a nuclear sub-image is calculated as the sum over all corresponding image points, each summand being assigned at least one of a large positive value if the compared image points both represent a relevant structure; being assigned a small value if only the image point of the ultrasound sub-image represents a relevant structure; and being assigned a large negative value if only the image point of the nuclear sub-image represents a relevant structure.

2. The method of claim 1 wherein the ultrasound image is a two-dimensional image which is identical to the respective ultrasound sub-images considered, and the nuclear sub-images are derived as two-dimensional nuclear sectional images from a three-dimensional medical nuclear image.

3. The method of claim 1 wherein the nuclear image of the body volume is acquired by means of at least one of a SPECT and a PET method.

4. The method of claim 1 wherein an estimated value is provided for the position of the ultrasound image relative to the body volume and that the calculation of the evaluation index takes into account only those relative positions of the nuclear image and the ultrasound image where the medical nuclear image occupies a position in a vicinity of this estimated value.

5. The method of claim 1 wherein a region is selected from the ultrasound image and that the evaluation index is calculated only for this region.

6. The method of claim 1 wherein the calculation of the evaluation index is performed for nuclear sub-images and ultrasound sub-images which have been at least one of stretched and compressed relative to one another in at least one dimension.

7. The method of claim 1 wherein the absolute values of one of the large positive and high negative values are larger as the image point values involved point more reliably towards the relevant structure.

8. A method of improving the resolution of a medical nuclear image of a body volume by combining it with an ultrasound image of the same body volume, the method comprising for various assumed relative positions of the nuclear medical image and the ultrasound image each time an evaluation index concerning the correspondence of a nuclear sub-image and an ultrasound sub-image of the same region of the body volume is calculated, and the relative position having the optimum value of the evaluation index is selected as the spatial registration position of the nuclear sub-image and the ultrasound sub-image; wherein wherever the corresponding image point values of the ultrasound sub-image are larger than a predetermined limit value, image points of the nuclear sub-image are reproduced in superposed form on the image points of the spatially registering ultrasound sub-image.

9. A device for the imaging of a body volume comprising:
a memory for an ultrasound image of the body volume;
a memory for a medical nuclear image of the body volume;
a data processing unit which is arranged to calculate, for various assumed positions of the medical nuclear image and the ultrasound image, an evaluation index concerning the correspondence of each time a nuclear sub-image and an ultrasound sub-image of the same region of the body volume and to select the relative position which has the optimum value of the evaluation index as the spatial registration position of the nuclear sub-image and the ultrasound sub-image; wherein wherever the corresponding image point values of the ultrasound sub-image are larger than a predetermined limit value, image points of the nuclear sub-image are reproduced in superposed form on the image points of the spatially registering ultrasound sub-image.

10. A method of improving the resolution of a medical nuclear image of a body volume by combining it with an ultrasound image of the same body volume, the method comprising;
calculating an evaluation index for various assumed relative positions of the nuclear medical image and the ultrasound image each time a correspondence of a nuclear sub-image and an ultrasound sub-image of the same region of the body volume; and
selecting the relative position having the optimum value of the evaluation index as a spatial registration position of the nuclear sub-image and the ultrasound sub-image;
wherein the evaluation index between an ultrasound sub-image and a nuclear sub-image is calculated as the sum over all corresponding image points, each summand being assigned at least one of a large positive value if the compared image points both represent a relevant structure; being assigned a small value if only the image point of the ultrasound sub-image represents a relevant structure; and being assigned a negative value if only the image point of the nuclear sub-image represents a relevant structure.

11. The method of claim 10 wherein the ultrasound image is a two-dimensional image which is substantially similar to the respective considered ultrasound sub-images, and the nuclear sub-images are derived as two-dimensional nuclear sectional images from a three-dimensional medical nuclear image.

12. The method of claim 10 wherein an estimated value is provided for the position of the ultrasound image relative to the body volume and the calculation of the evaluation index takes into account only those relative positions of the nuclear image and the ultrasound image where the medical nuclear image occupies a position in a vicinity of this estimated value.

13. The method of claim 10 wherein a region is selected from the ultrasound image and the evaluation index is calculated for this region.

14. The method of claim 10 wherein the calculation of the evaluation index is performed for nuclear sub-images and ultrasound sub-images which have been at least one of stretched and compressed relative to one another in at least one dimension.

15. The method of claim 10 wherein the absolute values of one of the large positive and large negative values are larger as the image point values involved point more reliably towards the relevant structure.

16. A method of improving the resolution of a medical nuclear image of a body volume by combining it with an ultrasound image of the same body volume, the method comprising;
   calculating an evaluation index for various assumed relative positions of the nuclear medical image and the ultrasound image each time a correspondence of a nuclear sub-image and an ultrasound sub-image of the same region of the body volume; and
   selecting the relative position having the optimum value of the evaluation index as a spatial registration position of the nuclear sub-image and the ultrasound sub-image;
   wherein wherever the corresponding image point values of the ultrasound sub-image are larger than a predetermined limit value, image points of the nuclear sub-image are reproduced in superposed form on the image points of the spatially registering ultrasound sub-image.

17. A medical imaging method comprising:
   acquiring nuclear med jeine image data;
   acquiring ultrasound image data.; and
   selecting a nuclear medicine image data set that best correlates to the ultrasound image data by comparing nuclear subimage data with the ultrasound image data and creating an index value based on high values for data that correlates and low values for data that does not correlate;
   wherein the index value is calculated as the sum over all corresponding image data, each summand being assigned at least one of a large positive value if the compared image data both represent a relevant structure; being assigned a small value if only the image data of the ultrasound image data represents relevant structure; being assigned a negative value if only the image point of the nuclear subimage data represents a relevant structure.

18. The medical imaging method of claim 17 further comprising creating an overlay of the selected nuclear medicine image data set and the ultrasound image data.

19. The medical imaging method of claim 17 further comprising inputting an estimated spatial position of the acquired ultrasound image data and nuclear subimage data proximate to the estimated spatial position is used to determine the nuclear medicine image data set that best correlates to the ultrasound image data.

* * * * *